United States Patent

Frater et al.

[11] Patent Number: 5,635,471
[45] Date of Patent: Jun. 3, 1997

[54] ODORANTS

[75] Inventors: Georg Frater, Winterthur; Urs Müller, Zurich; Martin Petrzilka, Wetzikon, all of Switzerland

[73] Assignee: Givaudan-Roure (International) SA, Vernier-Geneve, Switzerland

[21] Appl. No.: 398,726

[22] Filed: Mar. 6, 1995

[30] Foreign Application Priority Data

Mar. 10, 1994 [CH] Switzerland ............................. 708/94

[51] Int. Cl.$^6$ ...................................................... A61K 7/46
[52] U.S. Cl. .............................. 512/13; 549/385; 568/808
[58] Field of Search ............................. 549/385; 512/13; 568/808

[56] References Cited

U.S. PATENT DOCUMENTS 3,910,984 10/1975 Nussim et al. ..................... 260/465 D
4,162,256 7/1979 Sprecker et al. ........................ 252/522
5,376,630 12/1994 Sprecker et al. ........................ 512/14

OTHER PUBLICATIONS

S. Arctander, *Perfume and Flavor Chemicals I*, item 1581, (Montclair, NJ, 1969).

*Primary Examiner*—Amelia Owens
*Attorney, Agent, or Firm*—George W. Johnston; Catherine R. Smith; Mark E. Waddell

[57] ABSTRACT

The invention is concerned with the 7R/7S-diastereoisomer mixture of the formula

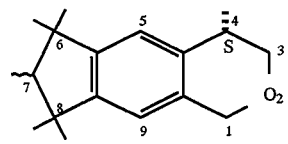

in pure form, essentially free of the corresponding (4R)-isomers.

The invention also concerns the 2R/2S-diastereoisomer mixture of the formula

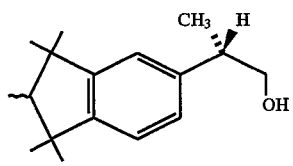

in pure form which is useful as an intermediate for producing I.

In addition, the invention concerns a process for obtaining I by subjecting II to isochromane ring closure. Odorant compositions containing I and the use of I as an odorant are also described.

4 Claims, No Drawings

ODORANTS

FIELD OF THE INVENTION

The invention is concerned with a novel odorant, namely the 7R/7S-diastereoisomer mixture of the formula

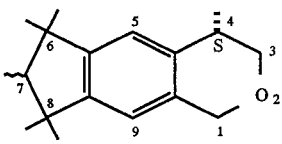

in pure form, wherein "S" indicates that the diastereoisomers are in the S-configuration at position 4. The invention also concerns the 2R/2S-diastereoisomer mixture of the formula

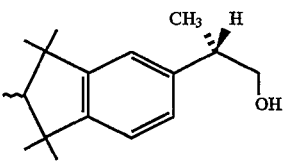

in pure form.

Additionally, the invention concerns odorant compositions containing I and the use of I as an odorant.

BACKGROUND

The mixture of two racemates of the formula I', below, is commercially available.

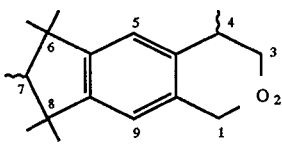

see S. Arctander, Perfume and Flavor Chemicals I, Montclair, N.J. 1969, item 1581. As is apparent from the structure of I', there are asymmetric carbon atoms at positions 4 and 7. Since the structure can be either in the R- or S- configuration at each of the asymmetric carbon atoms, there are four diastereoisomers corresponding to formula I' in the known commercially available mixture.

SUMMARY OF THE INVENTION

In accordance with the invention, a stereoselective process has been found for synthesizing the 7R/7S-diastereoisomer mixture of the formula

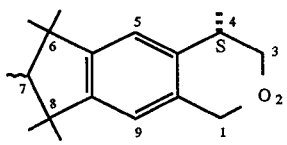

in pure form, wherein "S" indicates that the diastereoisomers are in the S-configuration at position 4. The invention also concerns the 2R/2S-diastereoisomer mixture of the formula

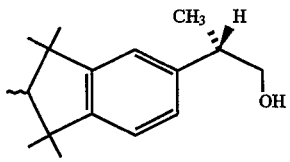

in pure form which is useful as an intermediate for producing I.

The process involves subjecting the 2R/2S-diastereoisomer mixture of the formula

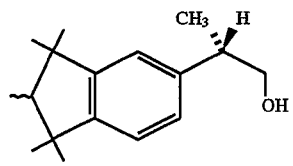

to an isochromane ring closure.

Additionally, the invention concerns odorant compositions containing I and the use of I as an odorant.

DETAILED DESCRIPTION

Mixture I is accessible according to the following Scheme:

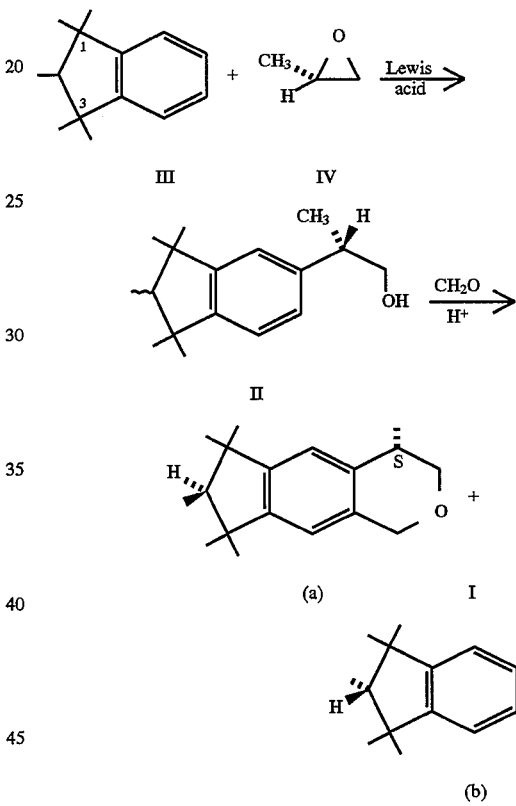

The isochromane ring closure of II is preferably carried out using formaldehyde or a synthetic analogue thereof, e.g. the acetal, especially the dimethyl or diethyl acetal or also dihexyl acetal. The reaction conditions are as follows:

Temperature: preferably lies between about 0° C. and about 200° C., most preferably between about 85° C. and about 150° C..

Catalyst: a protonic acid, for example p-toluenesulphonic acid or phosphoric acid, etc.

Acid concentration: 1 to 100% (wt./wt.) of the amount of II:

Ratio II:$CH_2O$: about 0.1-about 1.

The acetal can also be prepared in situ from $CH_2O$ and a lower alkanol.

Conditions which are well-known also apply to the Friedel-Crafts reaction of III to II, for example:

Lewis acid: especially $AlCl_3$, but also $SnCl_4$, $SnBr_4$, $TiCl_4$, $BCl_3$, etc.

Temperature range: about −30° C. for about +30° C., especially about −20° C. for about −0° C.
Solvent: saturated aliphatic, optionally halogenated hydrocarbon, for example pentane or hexane, etc., but also the usual, optionally halogenated aromatics, or also $CS_2$.
Ratio solvent to III: about 1:10 to about 10:1.
Ratio catalyst:IV: about 1:1 to about 2:1.
Ratio III:IV about 1:1 to about 10:1.
Working up: addition of an alkanol or aliphatic ether or also mixtures of such solvents, etc. to the reaction mixture. Unless otherwise indicated, ratios are expressed as molar ratios.

The diastereoisomer mixture I has very surprising properties.

Compared with the commercial mixture of the two racemates of the formula

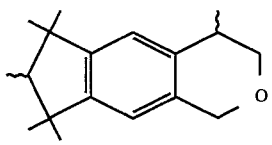   I' its use is very much preferred, which will be immediately evident from the following comparison of all corresponding olfactory threshold values:

| | | | |
|---|---|---|---|
| (4S)-cis isomer | 0.3 ng/l | air | I (b) |
| (4S)-trans isomer | 0.6 ng/l | air | I (a) |
| (4R)-cis isomer | 200 ng/l | air | |
| (4R)-trans isomer | 400 ng/l | air. | |

I'

On the other hand, the corresponding value for I' is 1.7 ng/l.

By using I, entrainment of about 50%. of unnecessary and completely functionless ballast is avoided in all cases. The term "mixture I in pure form" thus serves in the present case to distinguish this mixture I from the commercial product of formula I' above. It is intended to encompass not only the isolated 7R/7S-diastereoisomer mixture of the formula

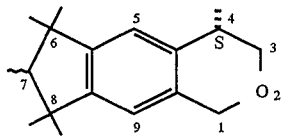   I but, in addition, mixtures that are essentially free of the mixture of (4 R)-isomers found in I', i.e. wherein the (4R)-isomers are present in only minor amount.

In other respects, the mixture I can be used as an odorant in exactly the same manner as the known isochromane musk substance, the indene I', although corresponding to the above olfactory threshold values only much lower concentrations of I would be required.

EXAMPLE a) 7.5 g of $AlCl_3$ were added to a solution, cooled to −10° C., of 26.2 g of 1,1,2,3,3-pentamethylindane in 15 ml of $CS_2$ to yield a yellow-brown mixture. 2.4 g of S (−)-propylene oxide dissolved in 2.5 ml of $CS_2$ were then slowly added to the yellow-brown mixture at −5° C. to −3° C. After completion of the addition the mixture was stirred at 0° C. for a further 30 minutes and then added to ice-water. Working up was effected by taking up in a mixture of hexane-tert.butyl methyl ether in the ratio 1:1.

The crude product was first distilled at 180°—200° C. and at 0.1 mm Hg, and then purified further by crystallization, namely by crystallization from hexane.

The melting point of the product (2S,2'R,S)-2-1',1',2',3',3'-pentamethylindan-5'-yl-propan-1-ol was 73°–74° C., $[a]_D^{22}(C_2H_5OH, c=1.0)$–6.23°.

b) The 2-indan-5'-yl-propan-1-ol obtained under a) was treated with paraformaldehyde, 1-hexanol and phosphoric acid exactly according to the procedure of Example 2 of U.S. Pat. No. 3,910,984 and the product, namely (4S,7RS)-1,3,4,6,7,8-hexahydro-4,6,6,7,8,8-hexamethyl-cyclopenta[g]-2-benzopyran, was obtained in good yield. $[a]_D^{22}(C_2H_5OH, c=1.18)$+21.4°.

We claim:
1. A 7R/7S-diastereoisomer mixture of the formula

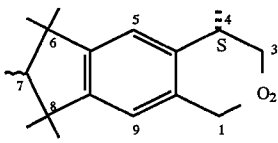   I in pure form, essentially free of the corresponding (4R)-isomers.

2. A 2R/2S-diastereoisomer mixture of the formula

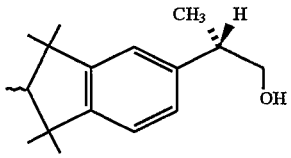   II in pure form.

3. An odorant composition, which contains the diastereoisomer mixture of formula I according to claim 1.

4. A process for the manufacture of the diastereoisomer mixture of formula I according to claim 1, which process comprises subjecting a 2R/2S-diastereoisomer mixture of the formula

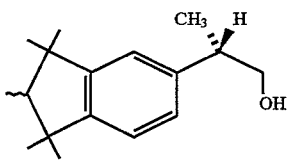   II to an isochromane ring closure by means of formaldehyde or a synthetic analog thereof in the presence of a protonic acid as catalyst at temperatures between 0° C. and 200° C.

* * * * *